(12) United States Patent
Liddell et al.

(10) Patent No.: US 12,697,479 B1
(45) Date of Patent: Aug. 4, 2026

(54) URETHRAL FLOW CONTROL VALVE AND SYSTEM AND METHODS THEREOF

(71) Applicants: Norman E. Liddell, Sevierville, TN (US); Dianne M. Liddell, Sevierville, TN (US)

(72) Inventors: Norman E. Liddell, Sevierville, TN (US); Dianne M. Liddell, Sevierville, TN (US)

( * ) Notice: Subject to any disclaimer, the term of this patent is extended or adjusted under 35 U.S.C. 154(b) by 0 days.

(21) Appl. No.: 19/176,161

(22) Filed: Apr. 11, 2025

(51) Int. Cl.
*A61B 5/20* (2006.01)
*A61M 39/24* (2006.01)

(52) U.S. Cl.
CPC ............ *A61M 39/24* (2013.01); *A61B 5/205* (2013.01); *A61M 2039/248* (2013.01)

(58) Field of Classification Search
CPC ......... A61B 5/205; A61B 5/208; A61B 5/036; A61B 5/03; A61B 5/204; A61B 5/746; A61B 5/0002; A61B 2562/0247; A61B 5/6874; A61M 2039/248; A61M 39/24; A61M 2205/3331; A61M 2205/3334; A61M 2210/1085; A61M 2202/0496
See application file for complete search history.

(56) References Cited

U.S. PATENT DOCUMENTS

| | | | | |
|---|---|---|---|---|
| 5,807,278 | A | * 9/1998 | McRae | A61B 5/4381 |
| | | | | 600/573 |
| 2016/0095684 | A1 | * 4/2016 | Berryman | A61L 15/40 |
| | | | | 600/29 |

* cited by examiner

*Primary Examiner* — Kai H Weng
(74) *Attorney, Agent, or Firm* — Hoang Steve Ngo

(57) ABSTRACT

A preferred embodiment of the present invention is a system composed of several devices that function together to selectively, on demand, control the flow of urine through the urethra. A valve also permits catheter-based elective or emergency instrumentation of the upper urinary tract without removal of the valve from the urethra. One aspect of the present invention is a body-implanted, coordinating system of devices for managing urine flow from a patient's urinary bladder through the urethra to the external environment primarily to prevent urinary incontinence with its sequelae. Another aspect of the present invention is a method or process for managing urine flow through a patient's urethra to prevent untimely and unintended incontinence of urine. The function and specific design of the valve assembly disclosed herein permits catheter-based elective or emergency instrumentation of the upper urinary tract without removal of the valve from the urethra.

5 Claims, 4 Drawing Sheets

URETHRAL FLOW CONTROL VALVE AND SYSTEM AND METHODS THEREOF

TECHNICAL FIELD OF THE INVENTION

The present invention relates in general to healthcare products, and more particularly, to a system to control urinary flow in the lower urinary tract.

BACKGROUND OF THE INVENTION

Incontinence of urine is a disease condition that can affect both males and females at any age, but becomes a chronic, life-changing, difficult-to-control problem primarily by those patients over age 60 that develop a variety of maladies that affect the urinary system. Some of the many reasons for developing incontinence include degeneration of tissues in the circulatory and nervous systems, hormonal and metabolism changes, cancers, and medical/surgical interventions. More specific examples include diabetes mellitus, Parkinson's disease, Alzheimer's and other dementias, infections, heavy metal poisoning, certain medications, cerebrovascular accidents, other injuries to the brain/spinal cord, spina bifida, some major surgeries (especially prostatectomy), and multiple sclerosis. Incontinence may also occur when involuntary muscles of the urinary bladder lose strength or sphincter muscles lose control resulting in continuous or intermittent leakage of urine. It has been said that an estimated 15% to 35% of the population over age 60 are prone to this problem, and these percentages tend to advance with age. In women, incontinence can increase with greater frequency than in men because of the effects of pregnancy and childbirth as well as menopause. Weak bladder sphincters, nerve damage, overactive bladder muscles, and a shorter urethra may all contribute to leakage. Types of urinary incontinence have been listed as stress incontinence (particularly from fluctuating and increased abdominal pressure), urge incontinence, overactive and neurogenic bladder, functional incontinence, overflow incontinence, transient incontinence, and a possible mixture of these types.

The uncontrolled passage of urine has many untoward and possibly serious medical as well as psychological effects, including but not limited to infection, dehydration, disruption of normal daily routines, offensive odors, inconvenience, embarrassment, frustration, anger, self-isolation, and depression. There are also increased economic losses: having to purchase and wear disposable incontinence-absorbing pads or clothing with its accompanying landfill or other types of waste disposal requirement; treating skin and other infections, some of which may originate from use of indwelling catheters and urine collection bags; use of uncomfortable external penile clamps which are not always reliable in preventing incontinence and can cause pain, tissue ischemia, and necrosis; and even the requirement for patient transfer to assisted living or other care facilities.

Some of the above-referenced causes of incontinence have had treatments invented or devised, while many are not yet satisfactorily remedied, and are thus ongoing for a considerable portion of the population and a source of significant emotional and physical distress. One particular device to prevent urinary incontinence has been marketed for males for approximately 40 years; but it requires a demanding implant surgery, can be difficult for some elderly patients to manipulate and utilize, and has had reliability problems, including device failure requiring replacement. In view of the above discussions, we offer the argument that there is still a need for a reliable, simple and relatively convenient to use, implantable treatment modality to safely and dependably control the flow of urine through the urethra when needed and demanded. One objective of this invention is to provide such a device, process, and method of urine flow control.

Despite the many years and large volume of research and development efforts by scientists and engineers and funding applied to efforts for control of urinary incontinence, a myriad of device designs yet a dearth of successful, marketable therapies has resulted. It may therefore still be useful to consider additional devices which can be implanted surgically and otherwise invasively to prevent unintended release of urine. Several experts in this field have included magnets as part of their invention proposals, many U.S. patents of which are enumerated and discussed briefly by Helms et al. in their U.S. Pat. No. 11,583,380 B1, the information and lessons of which are incorporated in this document by reference. Other uses of magnets in devices for controlling urine flow are found in a corrected publication, Pub. No.: US 2024/0225808 A9, by Wm. Howes, the disclosure and teachings of which are incorporated herein by reference. Furthermore, the current website, https://www.merriam-webster.com/dictionary/is incorporated herein by reference in its entirety for definitions of words and terms used herein.

SUMMARY OF THE INVENTION

The preferred embodiment of the invention is a system composed of several devices that function together to selectively, on demand, control the flow of urine through the urethra. The valve also permits catheter-based elective or emergency instrumentation of the upper urinary tract without removal of the valve from the urethra.

More specifically, one aspect of the present invention is a body-implanted, coordinating system of devices for managing urine flow from a patient's urinary bladder through the urethra to the external environment primarily to prevent urinary incontinence with its sequelae. Another more specific aspect of this current invention is a method or process for managing urine flow through a patient's urethra to prevent untimely and unintended incontinence of urine.

The function and specific design of the valve assembly disclosed herein permits catheter-based elective or emergency instrumentation of the upper urinary tract without removal of the valve from the urethra. The present invention including the preferred and alternative embodiments have been considered with the above noted desired objectives in mind. Those skilled in the art will understand many benefits from the embodiment described herein and it is intended that all of those benefits are to be included and encompassed by this disclosure.

US 12,697,479 B1

Figures 4, 5:
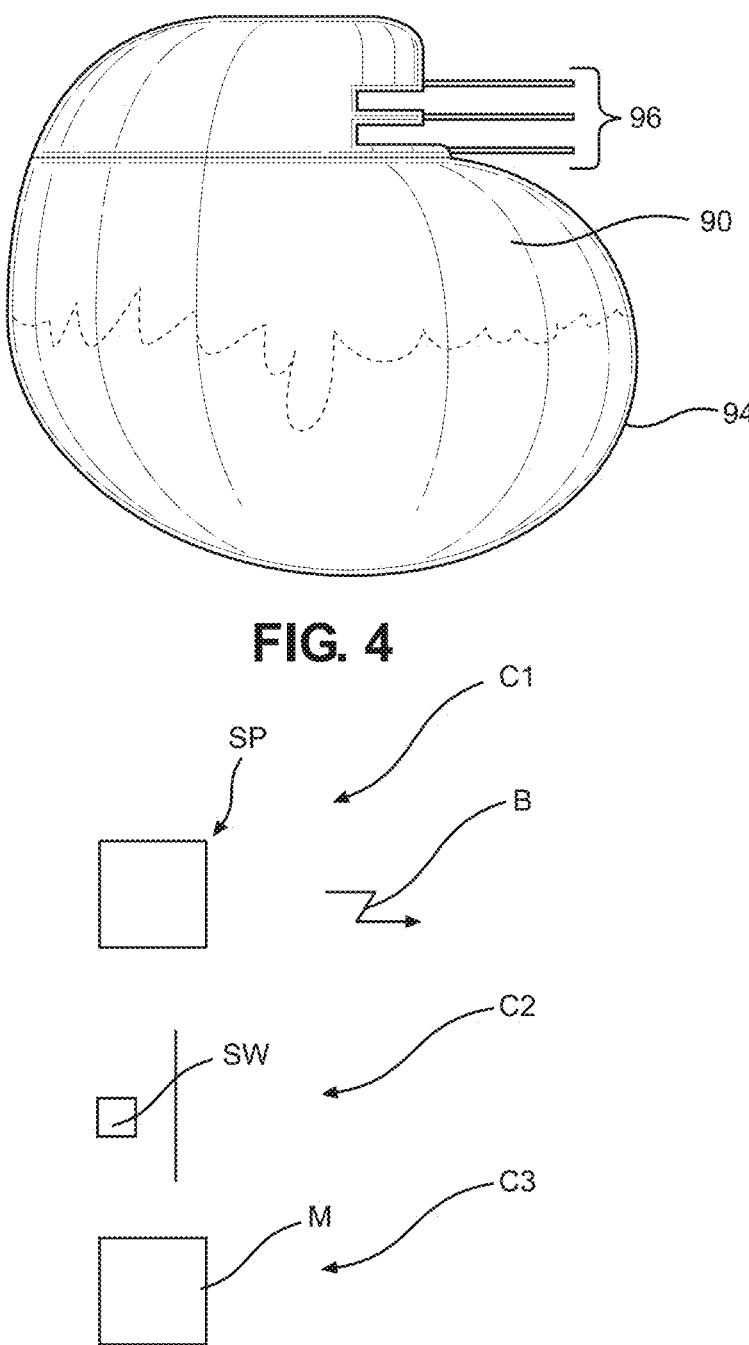

FIG. 4 shows a generalized figure of the case containing the battery and electronic control circuitry; and FIG. 5 illustrates variations of valve control means.

DETAILED DESCRIPTION OF THE PREFERRED EMBODIMENT OF THE INVENTION

These and other aspects of the invention will be apparent to one skilled in the art upon reading the following detailed description and accompanying figures. While the invention is susceptible to various modifications and alternative forms, specific embodiments thereof will be described in detail and shown by way of example. It should be understood, however, that it is not intended to limit the invention to the particular forms disclosed, but, on the contrary, the invention is to cover all modifications and alternatives falling within the spirit and scope of the invention as described and taught herein.

Figure 1:
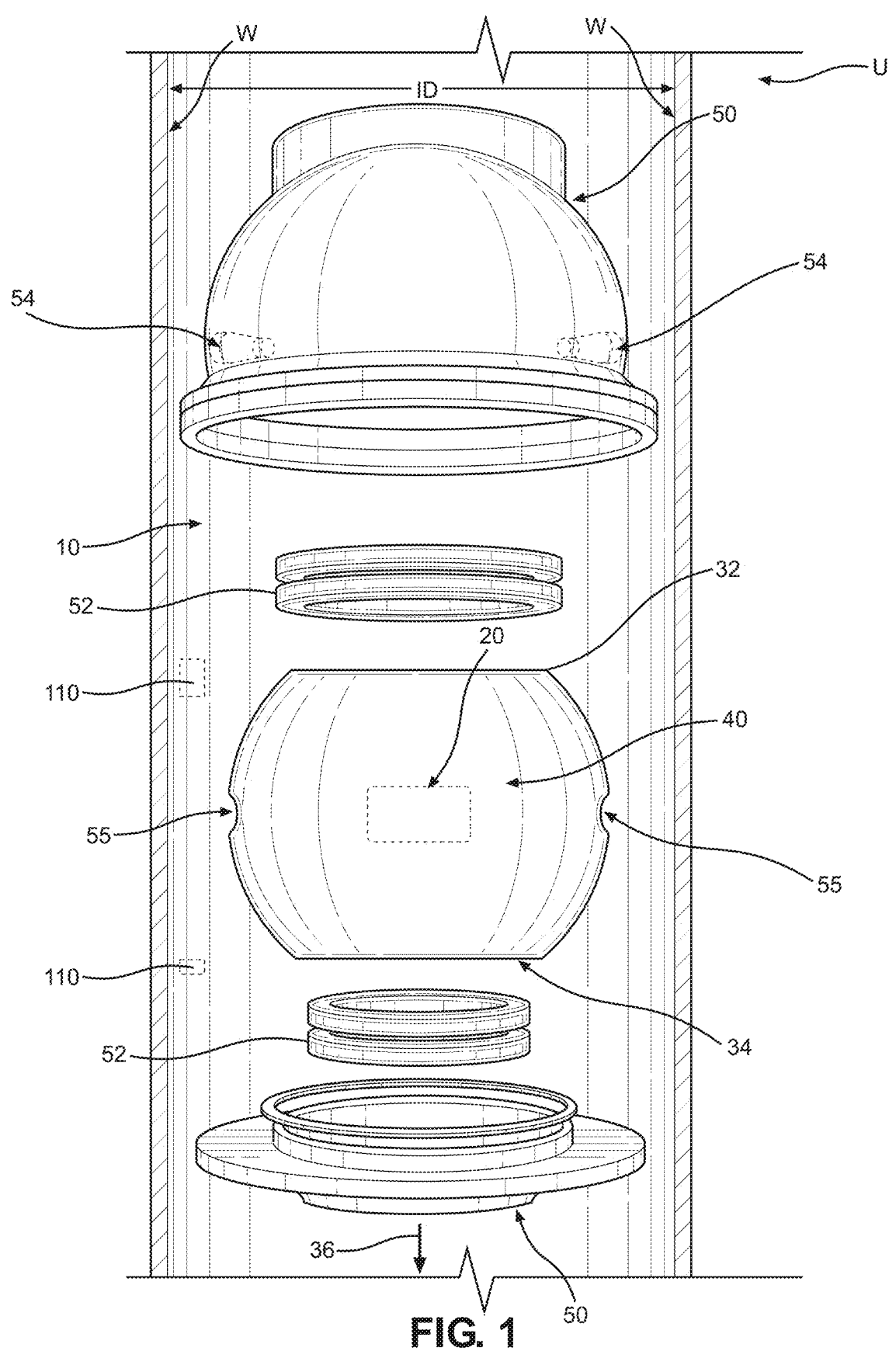
FIG. 1 shows a lateral, exploded view of the valve's preferred embodiment as designed for insertion into the urethra according to the descriptions and teachings in this document.
Figures 2A, 2B:
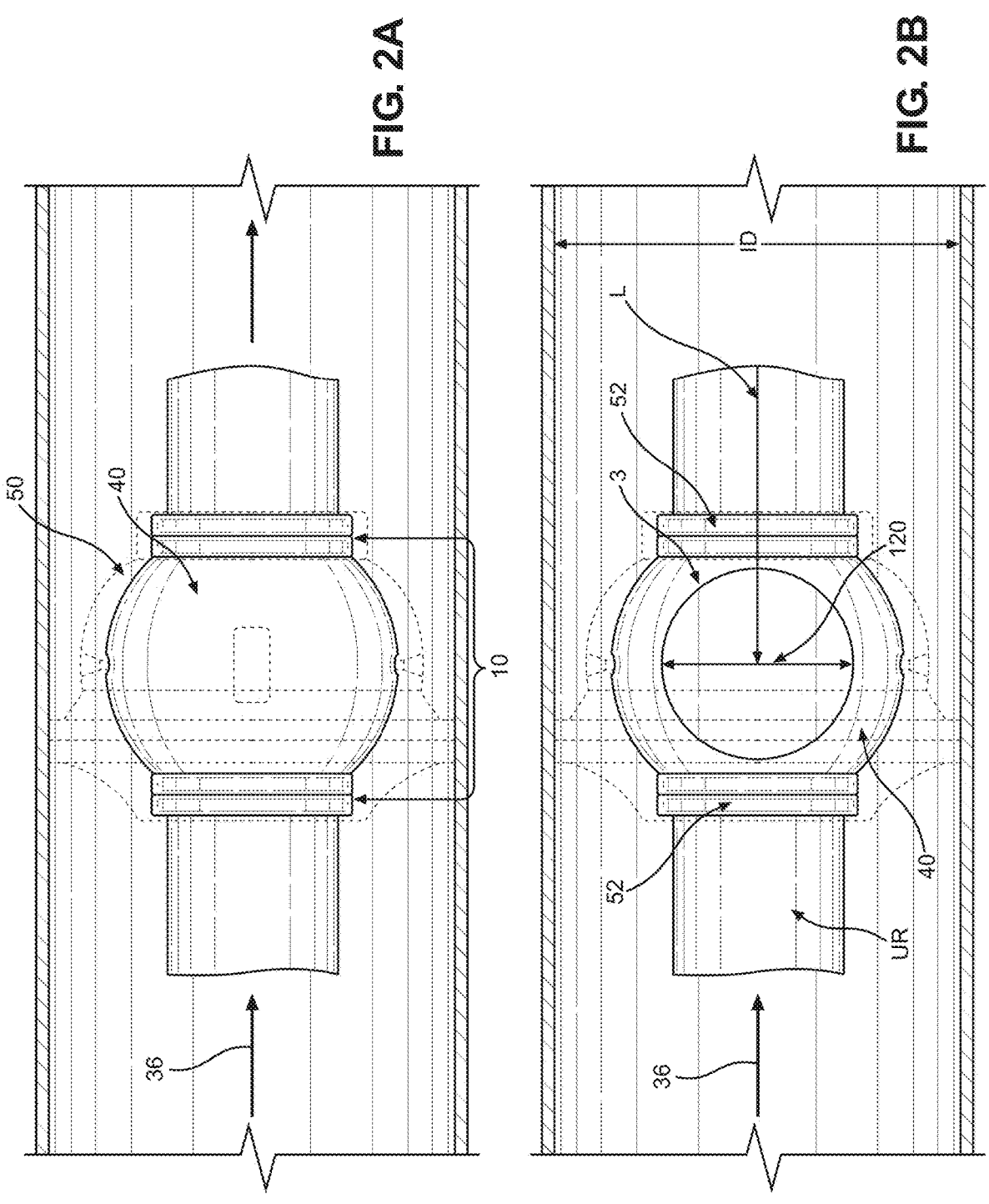
FIG. 2A shows a lateral cutaway view of the valve, function within a urethra, with the valve in the open position.
FIG. 2B shows a lateral cutaway view of the valve, function within a urethra, with the valve in the closed position and fluid flowing against the ball.

Referring to the figures, the present invention is embodied in valve 10 which is uniquely modified trunnion-mounted ball valve, having trunnions 54 (FIGS. 1 and 3) in seats 55 defined in body (FIGS. 1 and 3) of ball 40, which is constructed of biocompatible, durable materials, highly resistant to wear and degradation by chemicals found in urine. By example, some of these materials may include polymers, such as polytetrafluoroethylene (PTFE) or corrosion proof hybrid metal alloys. A magnet, such as permanent strong magnet 20, preferably neodymium, or a ferromagnetic metal strip would be molded into wall of either the 'leading' 32 or the 'trailing' 34 half of ball 40. Valve body 50 for ball 40 and seats 52 may be constructed of the same material as the ball itself or other selected compatible materials permit the ball to rotate smoothly and securely through a 90° arc to control urine flow. The diameter 120 of the lumen L (FIG. 2B) of the ball itself is of sufficient size to permit the possible necessary future passage of any catheter-based instruments or other devices or medications needed for diagnosis or treatment of any of the organs upstream from the urethra, including the bladder, ureters, or kidneys. FIG. 2B shows the valve in the closed position with urine UR in lumen L upstream of the valve assembly. The outside diameter of the valve body 50 will be somewhat larger than the interior diameter ID (FIGS. 1 and 2B) of the urethra U as measured between urethra walls W so as to slightly stretch interior diameter ID of the urethra at the final resting position of insertion of the valve. This valve assembly 10 would be sized and inserted based on the urethra lumen size ID (see FIG. 1) under local anesthesia and sterile conditions into the urethra to a desirable position as determined by the operating practitioner.

The preferred form of valve body 50 is constructed of a biocompatible material and is actually one piece with the ball and sealing seats enclosed within. The trunnions 54 are in the form of support pins permanently affixed in the valve body and with their exposed tips placed in depressions in the center of the ball's surface to stabilize the ball's position and allow its 90° rotation, on electromagnetic activation, in one direction to open the valve and in the other direction to close the valve. A permanent magnet 20 (FIG. 3), that interacts with activated electromagnets 80 and 84, is embedded in the wall of the ball.

Figure 3:
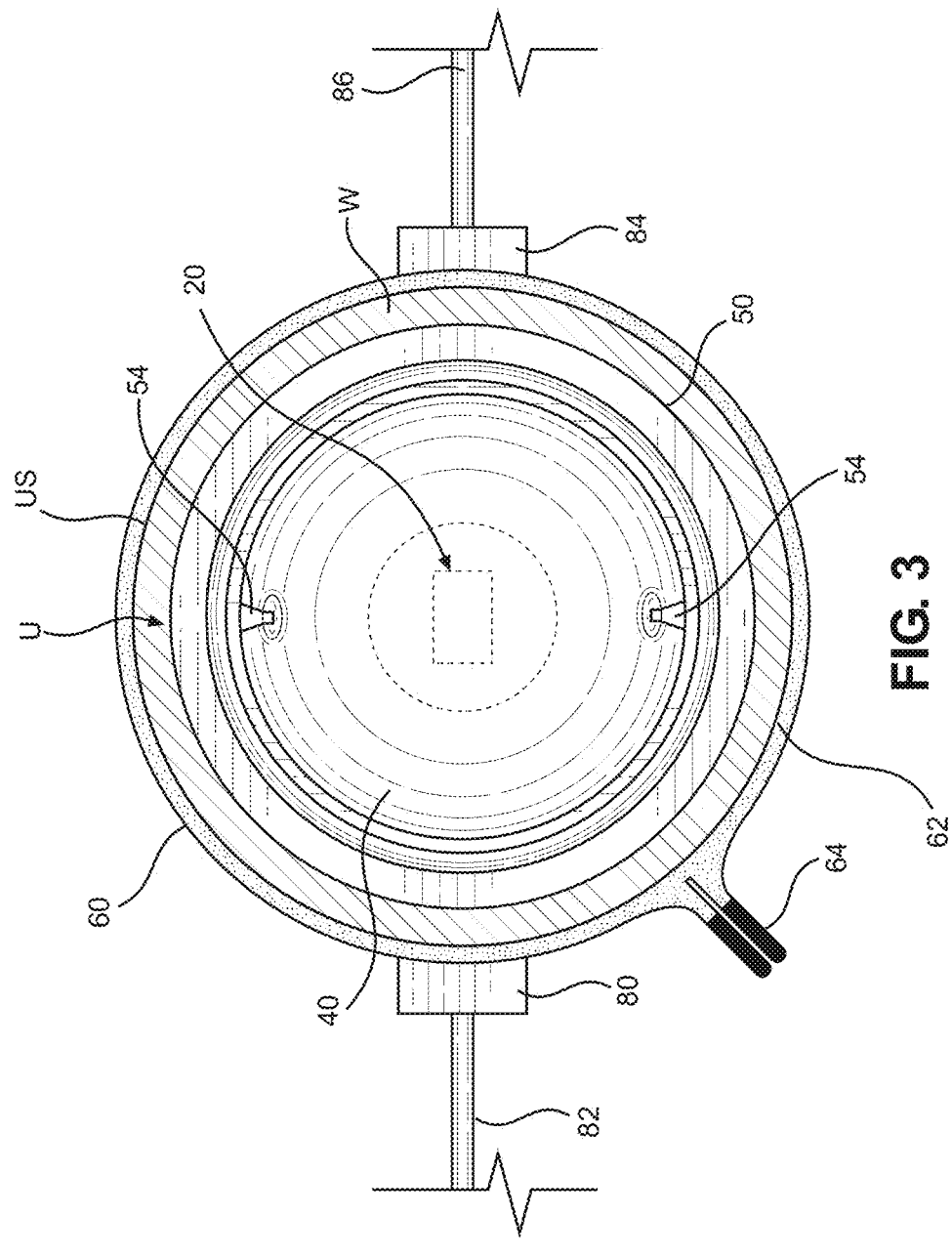
FIG. 3 Illustrates the valve in the closed position as it appears from the effluent (downstream) view.

As indicated in the figures, permanent magnet 20 is embedded in the center of the surface of ball 40. Also shown in FIG. 3 is a stabilizing ring 60, composed of soft biocompatible material, around the outer (visceral) wall W of the urethra U, with electromagnets 80 and 84 attached thereto and their leads 82 and 86 that are connected to battery case 94 by lead portals 96 to be electrically connected to a battery 90 and appropriate electronic circuitry. Stabilizing ring 60, leads 82 and 86, and battery 90 and battery case 94 are all implanted surgically, ideally during the same procedure with insertion of the valve into the urethra. The electromagnets are fused to the stabilizing ring 180° from one another and are positioned to pull the permanent magnet portion of the ball in opposite directions based upon which electromagnet is activated, thus opening or closing the valve. The stabilizing ring around the exterior surface of the urethra also assists in preventing the valve from migrating in either direction inside the urethra and would gently press the wall of the urethra against the surface of the valve thereby preventing leakage around the valve.

A second aspect of the application of the above-described valve assembly 10 is to apply, most likely by robotically-assisted surgical technique, split stabilizing ring 60 (FIG. 3) circumferentially around the visceral or outside surface US of the urethra U at the location of the previously inserted valve body. The preferred form of the stabilizing ring has a concave cross-section with each of the two edges 62 of the ring of somewhat smaller diameter than the center of the ring so that it fits snugly around the visceral surface S of the urethra at the location where the valve body had been placed. This stabilizing ring functions to prevent migration up or down the urethra, tilting from precise cross-sectional alignment, or other misalignment of the valve body within the urethra. The preferred form of the stabilizing ring is composed of a biocompatible material shaped and applied firmly enough to prevent change in position of the valve body within the lumen of the urethra yet also avoid compromising vital circulation to the urethral tissue. The stabilizing ring has suture wings 64 to not only affix the stabilizing ring in position around the urethra but also to make available additional fixation to appropriate surrounding tissue to further stabilize the position of the valve to prevent migration of the valve assembly during its function as described elsewhere in this disclosure. It is understood that the compatibility of applying this device design to this type of body tissue optionally would be determined at the time of development and use by those well skilled in the technique and art of this type of surgical implantation. Other mechanisms or devices may be found to be more appropriate or efficient during development of this device and be added.

As shown in FIG. 3, an electromagnet 80 is permanently fused to the stabilizing ring (FIG. 3) in an appropriate position to cause optimal rotation of the valve's ball to cause it to function as intended (open and close completely). Magnet 80 includes electrical leads 82 connected to surgically implanted battery 90 (not shown in FIG. 3) similar in size to that used for a cardiac pacemaker, placed in an appropriate location determined by the surgeon. Electromagnet 84 with lead 86 is fused in a position on stabilizing ring 60 circumferentially about 180° away from electromagnet 80, and also connected to the battery via a separate lead 86. All elements of the electronic circuitry, including the electromagnets and leads, would be sealed and isolated from the surrounding tissue by a biocompatible material such as silicone rubber coating, for example, as has been done with cardiac pacemaker lead connections. Battery 90 and its associated electronic circuitry including lead portals would be contained in a sealed metal case (FIG. 4) and are able to receive Bluetooth signals to separately and selectively operate the electromagnets. Functioning to open and close the valve would require a single pulsed stimulation of the electromagnets that causes them to interact with the magnet in the valve's ball and cause it to rotate 90° and open or close the valve based on programming of the circuit function. The single pulse function, rather than a continuous current flow to keep the valve open or closed, should extend battery life considerably before replacement is required. This type of valve, widely used and reliably functioning long-term in many other applications, is also referred to as a "90-degree shut off valve." Further disclosure of the details of this valve are known to those skilled in the art based on the teaching of this disclosure and thus will not be described herein. The "closed" position would of course be the default position to prevent incontinence; a patient or attendant could choose to trigger the opening of the valve to allow micturition.

Another embodiment involving the description outlined above would be addition of one or more retention magnets 110 to ensure that the open position and a closed position are retained.

As illustrated in FIG. 5, circuitry in the battery assembly could be designed to allow three optional ways to operate the valve. One circuit design C1 would use Bluetooth® signaling B from a smart phone SP or other such wireless signaling devices to deliver electronic pulses to the electromagnets. A second option C2 could be a subcutaneously located manual pressure switch SW to send electronic stimuli from the battery to the electromagnets alternately to open or close the valve; and a third source C3 of valve control may be from a strong, handheld magnet M such as neodymium) to briefly hold over the battery implant location to stimulate yet another type of switching circuitry, that can be programmed into the battery's electronics to open and close the valve. All three of these elective flow control options can be programmed to coexist in the same battery circuit assembly yet operate independently.

The first description of the valve unit in use will be presented in association with a Bluetooth® operation. When a Bluetooth® signal is sent from a cell phone or other wireless signaling device and received by the electronic circuitry (located in the subcutaneously implanted battery case), a corresponding single electrical impulse is directed from the battery through leads, attached between the battery case and the electromagnets, to cause those electromagnets to be immediately activated by the single electrical stimulus to selectively open or close the valve.

Two other methods of activating the electromagnets could be included in the design of this device by (1) subcutaneously implanting a simple pressure activated on-off switch, connecting it to the battery case, and additionally programming the electronics function. The patient would simply press the area over the implanted switch to activate the valve function; or (2) additional programming of the electronics would allow holding a strong (neodymium) magnet briefly over the area where the battery case (electronic circuitry) had been implanted. These two optional means of activating the electromagnets would produce the same valve opening and closing functions.

The two electromagnets 80, 84 are attached on opposite sides of a stabilizer ring 60 (i.e., approximately 180° apart). The stabilizer ring surrounds the exterior of the urethra U at the point where the valve body 50 has been placed and serves two purposes:

1. It prevents the valve body within the urethra from moving from the position where it was inserted.
2. It holds the electromagnets in the appropriate positions to interact correctly with the permanent magnet, which is an integral part of the ball within the valve body.

The valve body holds the ball 40 between two seals 52 that prevent leakage around the ball when the valve is in a closed position. The ball is held in position by trunnion pins 54, on which the ball rotates with the activation of the electromagnets, to maintain alignment of hole 120 through the ball with the inflow and outflow tracts of the valve body, which are of course correspondingly aligned with the lumen of the urethra.

The valve function of opening and closing, to permit and restrict urine flow, is driven by the interaction of the electromagnets with the permanent magnet that is embedded within the surface of the ball. To close the open valve one of the electromagnets (when electrified) exhibits a polarity that repels the permanent magnet in the ball. Simultaneously the opposite electromagnet exhibits a polarity that attracts the permanent magnet, thereby causing a push-pull effect on the ball to cause it to rotate approximately 90°, which thereby makes the pathway through the ball unavailable (closed position) and prevents urine flow. Opening the valve merely requires another Bluetooth signal to the circuitry in the battery case to reverse the polarity of the electromagnets to turn the ball 90° in the opposite direction (from the closed position), thereby realigning the hole through the ball with the pathway through the valve body and permitting urine flow.

It is understood that while certain forms of the present invention have been illustrated and described herein, it is not to be limited to the specific forms or arrangements of parts described and shown.

What is claimed is:

1. A process for managing urine flow from a patient's bladder through the patient's urethra comprising the steps of:

placing a pressure sensor on the patient's bladder;

placing a moisture sensor on the patient's urethra;

providing a data management system;

providing the data management system with a pressure signal receiver;

providing the data management system with a moisture signal receiver;

providing a urethra closing valve on the patient's urethra;

providing a signal receiver in the urethra closing valve for receiving signals from the data management system;

providing a urethra closing valve activation system operably connected to the urethra closing valve signal receiver;

measuring pressure in the patient's bladder and generating a bladder pressure level signal;

transmitting a bladder pressure signal to the data management system and receiving the bladder pressure signal in the data management system;

measuring moisture level in the patient's urethra and generating a urethra moisture level signal;

transmitting the urethra moisture level signal to the data management system and receiving the urethra moisture level signal in the data management system;

activating the urethra closing valve and occluding the urethra when pressure in the bladder exceeds a preset value; and activating the urethra closing valve and occluding the patient's urethra when moisture in the patient's urethra exceeds a preset value.

2. The process according to claim 1, further including a step of activating the urethra closing valve when bladder pressure rises faster than a preset value.

3. The process according to claim 1, further including a step of activating the urethra closing valve when urethra moisture rises faster than a preset value.

4. The process according to claim 1, further including a step of manually activating the urethra closing valve.

5. The process according to claim 1, further including a step of activating an alert when the valve is closed.

* * * * *